(12) United States Patent
Ji et al.

(10) Patent No.: US 11,701,395 B2
(45) Date of Patent: Jul. 18, 2023

(54) **FOOD COMPOSITION AND PHARMACEUTICAL COMPOSITION FOR INHIBITING SJOGREN'S SYNDROME EACH CONTAINING *BIFIDOBACTERIUM PSEUDOCATENULATUM* C-RAPO (KCTC13986BP) AND *BIFIDOBACTERIUM BIFIDUM* ATT (KCTC13474BP)**

(71) Applicant: BIFIDO CO., LTD., Gangwon-do (KR)

(72) Inventors: Geun Eog Ji, Seoul (KR); Myeong Soo Park, Seoul (KR)

(73) Assignee: BIFIDO CO., LTD., Hongcheon-gun (KR)

( * ) Notice: Subject to any disclaimer, the term of this patent is extended or adjusted under 35 U.S.C. 154(b) by 51 days.

(21) Appl. No.: 17/574,399

(22) Filed: Jan. 12, 2022

(65) Prior Publication Data

US 2022/0211775 A1 Jul. 7, 2022

Related U.S. Application Data

(62) Division of application No. 16/946,658, filed on Jun. 30, 2020, now Pat. No. 11,253,555.

(30) Foreign Application Priority Data

Mar. 19, 2020 (KR) .......................... 10-2020-0033513

(51) Int. Cl.
| | |
|---|---|
| *A61K 35/745* | (2015.01) |
| *A61K 39/00* | (2006.01) |
| *A61K 39/05* | (2006.01) |
| *A61K 35/00* | (2006.01) |
| *A23L 33/00* | (2016.01) |
| *A23L 33/135* | (2016.01) |
| *A61P 37/02* | (2006.01) |
| *A61K 9/00* | (2006.01) |

(52) U.S. Cl.
CPC .......... *A61K 35/745* (2013.01); *A23L 33/135* (2016.08); *A23L 33/40* (2016.08); *A61K 9/0056* (2013.01); *A61K 39/05* (2013.01); *A61P 37/02* (2018.01); *A23V 2002/00* (2013.01); *A23Y 2300/25* (2013.01); *A23Y 2300/59* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 9,610,307 B2 | 4/2017 | Berry et al. | |
| 10,617,725 B2 * | 4/2020 | Ji | ........................... C12N 1/205 |

FOREIGN PATENT DOCUMENTS

| | | |
|---|---|---|
| KR | 10-2002-0033643 A | 5/2002 |
| KR | 10-2009-0043910 A | 5/2009 |
| KR | 10-2016-0115176 A | 10/2016 |
| KR | 10-2019-0014305 A | 2/2019 |
| KR | 10-2019-0059494 A | 5/2019 |
| KR | 10-1999259 B1 | 7/2019 |
| KR | 10-2019-0099360 A | 8/2019 |
| KR | 10-2019-0106578 A | 9/2019 |
| KR | 10-2069807 B1 | 1/2020 |
| KR | 10-2162470 B1 | 10/2020 |

OTHER PUBLICATIONS

Marcus C. de Goffau et al., "Fecal Microbiota Composition Differs Between Children With β-Cell Autoimmunity and Those Without", DIABETES, vol. 62, Apr. 2013, pp. 1238-1244 (7 pages total).
Machine translation of KR 102162470 B, pp. 1-11, 2020.
Moon et al., "Gut dysbiosis is prevailing in Sjogren's syndrome and is related to dry eye severity", PLoS ONE, 2020, vol. 15, No. 2, e0229029,14 pages.

* cited by examiner

*Primary Examiner* — S. Devi
(74) *Attorney, Agent, or Firm* — Sughrue Mion, PLLC (57) ABSTRACT

Disclosed are *Bifidobacterium pseudocatenulatum* C-RAPO (KCTC13986BP) and *Bifidobacterium bifidum* ATT (KCTC13474BP) strains that have the effects of inhibiting sialoadenitis, which is a symptom of the Sjogren's syndrome, and inhibiting a reduction in saliva flow rate. Based on this, these strains can be used for prevention or treatment of Sjogren's syndrome and can be developed into food, health food and pharmaceuticals.

4 Claims, 11 Drawing Sheets

FOOD COMPOSITION AND PHARMACEUTICAL COMPOSITION FOR INHIBITING SJOGREN'S SYNDROME EACH CONTAINING *BIFIDOBACTERIUM PSEUDOCATENULATUM* C-RAPO (KCTC13986BP) AND *BIFIDOBACTERIUM BIFIDUM* ATT (KCTC13474BP)

CROSS-REFERENCE TO RELATED APPLICATIONS

This application is a Rule 53(b) Divisional Application of U.S. application Ser. No. 16/946,658 filed Jun. 30, 2020, now U.S. Pat. No. 11,253,555, which claims priority to Korean Patent Application No. 10-10 2020-0033513 filed Mar. 19, 2020, the disclosures of which are incorporated herein by reference in their respective entireties.

BACKGROUND OF THE INVENTION

Field of the Invention

The present invention relates to a composition for inhibiting Sjogren's syndrome containing *Bifidobacterium pseudocatenulatum* C-RAPO (KCTC13986BP) and *Bifidobacterium bifidum* ATT (KCTC13474BP) strains. More particularly, the present invention relates to a food composition for inhibiting Sjogren's syndrome and a pharmaceutical composition for preventing or treating Sjogren's syndrome, each containing *Bifidobacterium pseudocatenulatum* C-RAPO (KCTC13986BP) and *Bifidobacterium bifidum* ATT (KCTC13474BP) strains.

Description of the Related Art

Sjogren's syndrome is a chronic autoimmune disease that causes symptoms of dry mouth and dry eyes due to the infiltration of lymphocytes into exocrine glands and thus the destruction of exocrine glands. Sjogren's syndrome is an autoimmune disease that can invade the whole body in addition to causing symptoms of dry mouth and dry eyes due to dysfunction of the exocrine gland, which may cause arthritis, lung invasion, kidney invasion, vasculitis, neuritis, malignant lymphoma and the like. The onset rate of malignant lymphoma is about 40 times higher than that of normal people of the same age, gender and race.

Although the pathogenesis of Sjogren's syndrome is not clearly found, at present it is known that autoantigens occur in epithelial cells in response to factors that can induce innate immune system activity, such as viruses, and antibodies to the autoantigens are produced, causing activation of abnormal autoimmunity due to the immune complex including immunoglobulin-autoantigens. In addition, Sjogren's syndrome is characterized by reduced sensitivity to calcium and neurotransmitters in the acinus, which is the terminal structure of the salivary gland, functioning to express the components of saliva and to release saliva, and by disorder of salivation due to the production of autoantibodies that attack the M3R receptor and the Aquaporin 5 receptor.

Sjogren's syndrome can occur at any age, including children, but increases predominantly in older age. The prevalence in women over 60 in foreign countries, excluding Korea, is about 2 to 3%, and the prevalence in Korea is also expected to increase as Korea becomes an aged society. The exact prevalence of Sjogren's syndrome is not known due to the lack of epidemiological investigations in Korea, but statistics of other countries (Greece and Sweden) show a prevalence of 0.3 to 3%.

There are no fundamental methods for treating Sjogren's syndrome and there is only supplementary drug therapy to alleviate the progression of symptoms in respective body areas and prevent complications. Dry mouth is often treated or alleviated by frequently drinking water, using spray-type artificial saliva producers or administering pilocarpine. Also, dry skin is treated or alleviated by sufficient moisturizing and administration of nonsteroidal anti-inflammatory analgesics to relieve inflammation. However, these are not fundamental methods for treating Sjogren's syndrome since they are of limited effectiveness and entail side effects. Therefore, there is an urgent need to develop an effective therapeutic agent for Sjogren's syndrome.

PRIOR ART

Patent Document

Korean Patent Laid-open No. 10-2016-0115176 (published on Oct. 6, 2016) teaches that the symptoms of Sjogren's syndrome can be alleviated by overexpressing PAX3 in a Sjogren's-syndrome-induced animal model, and discloses a composition for preventing and treating Sjogren's syndrome containing, as an active ingredient, PAX3 which inhibits the production of inflammatory cytokines.

Korean Patent Laid-open No. 10-2009-0043910 (published on May 7, 2009) discloses a composition containing anti-4-1BB for effectively preventing and treating Sjogren's syndrome and lupus.

Korean Patent Laid-open No. 10-2019-0106578 (published on Sep. 18, 2019) discloses a composition for preventing and treating Sjogren's syndrome containing butyrate and various uses thereof.

SUMMARY OF THE INVENTION

Therefore, the present invention has been made in order to solve the drawbacks with the prior art, and it is an object of the present invention to provide novel lactic acid bacteria having excellent Sjogren's syndrome efficacy, and a pharmaceutical composition and a food composition for preventing and treating Sjogren's syndrome.

In accordance with the present invention, the above and other objects can be accomplished by the provision of a food composition for inhibiting Sjogren's syndrome containing the strain *Bifidobacterium pseudocatenulatum* C-RAPO (KCTC13986BP).

In accordance with another aspect of the present invention, provided is a pharmaceutical composition for preventing or treating Sjogren's syndrome containing the strain *Bifidobacterium pseudocatenulatum* C-RAPO (KCTC13986BP).

In accordance with another aspect of the present invention, provided is a food composition for inhibiting Sjogren's syndrome containing the strain *Bifidobacterium bifidum* ATT (KCTC13474BP).

In accordance with another aspect of the present invention, provided is a pharmaceutical composition for preventing or treating Sjogren's syndrome containing the strain *Bifidobacterium bifidum* ATT (KCTC13474BP).

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

The present invention provides *Bifidobacterium pseudocatenulatum* C-RAPO (KCTC13986BP) and *Bifidobacterium bifidum* ATT (KCTC13474BP) strains. The experiment of the present invention shows that the *Bifidobacterium pseudocatenulatum* C-RAPO (KCTC13986BP) and *Bifidobacterium bifidum* ATT (KCTC13474BP) strains have effects of reducing inflammatory cell infiltration and increasing saliva secretion (SFR) in patients afflicted with Sjogren's syndrome. More specifically, the pathological analysis experiment involving salivary gland tissue H&E staining showed that a group administered with *Bifidobacterium pseudocatenulatum* C-RAPO (KCTC13986BP) as a test drug has had therapeutic effect on sialoadenitis when compared with a vehicle-administered group. The experiment of T-cell/B-cell infiltration analysis on salivary gland tissue showed that administration with 50 mg/kg/day of *Bifidobacterium pseudocatenulatum* C-RAPO (KCTC13986BP) decreases inflammatory cell infiltration, and thus decreases infiltration of T and B cells.

In addition, the saliva secretion (SFR) experiment demonstrated that administration with 50 mg/kg/day of *Bifidobacterium pseudocatenulatum* C-RAPO (KCTC13986BP) and *Bifidobacterium bifidum* ATT (KCTC13474BP) inhibits a reduction in saliva secretion, that is, a reduction in saliva secretion attributable to Sjogren's syndrome.

It was found that both *Bifidobacterium pseudocatenulatum* C-RAPO (KCTC13986BP) and *Bifidobacterium bifidum* ATT (KCTC13474BP) are effective in suppressing Sjogren's syndrome, but *Bifidobacterium pseudocatenulatum* C-RAPO (KCTC13986BP) is preferred due to its effects of treating sialoadenitis as well as inhibiting reduction of saliva secretion.

The present invention provides a food composition for inhibiting Sjogren's syndrome containing *Bifidobacterium pseudocatenulatum* C-RAPO (KCTC13986BP) and *Bifidobacterium bifidum* ATT (KCTC13474BP) strains.

In the present invention, the food composition is not necessarily limited to a certain formulation, and is, for example, a formulation of a capsule, tablet, powder, granule, liquid, pill, flake, paste, syrup, gel, jelly or bar. In addition, the food composition may be a general food form prepared by adding the same to food ingredients of beverages, teas, spices, chewing gum, confectioneries or the like.

The present invention provides a pharmaceutical composition for preventing or treating Sjogren's syndrome containing *Bifidobacterium pseudocatenulatum* C-RAPO (KCTC13986BP) and *Bifidobacterium bifidum* ATT (KCTC13474BP) strains.

Here, the pharmaceutical composition may be prepared in the form of various parenteral or oral formulations according to a known method, and a typical formulation for parenteral administration is a formulation for injection, such as an isotonic aqueous solution or suspension. The formulation for injection may be prepared according to techniques known in the art using a suitable dispersing agent or wetting agent and a suspending agent. For example, the formulation for injection can be prepared by dissolving each component in saline or buffer. In addition, oral formulations include, but are not limited to, powders, granules, tablets, pills, capsules and the like.

In addition, the pharmaceutical composition formulated by the method described above can be administered in an effective amount through various routes including oral, transdermal, subcutaneous, intravenous or intramuscular routes. The term "effective amount" refers to an amount that exhibits a prophylactic or therapeutic effect when administered to a patient. The dosage of the pharmaceutical composition according to the present invention can be appropriately selected according to the route of administration, the subject of administration, age, gender, weight, the condition of the subject, and disease severity.

Hereinafter, the configuration of the present invention will be described in more detail with reference to the following examples and experimental examples. The scope of the present invention is not limited to the examples and experimental examples, and includes modifications of the technical concept equivalent thereto.

The abbreviations are summarized and tabulated prior to the description of this experiment.

TABLE 1

| Abbreviations | Definition of Terms | Korean |
|---|---|---|
| B | *Bifidobacterium* | 비피도박테리움 |
| NOD | Non-obese diabetic | 비 비만 당뇨병 |
| Ig | Immunoglobulin | 면역글로불린 |
| SFR | Saliva flow rate | 타액 분비량 |
| ELISA | Enzyme-linked immunosorbent assay | 효소 면역 측정법 |
| CD | Cluster of differentiation | 세포표면항원무리(분화클러스터) |
| FSC-A | Forward scatter-Average | 전면 산란광 평균 |
| SSC-A | Side scatter-Average | 측면 산란광 평균 |
| PMA | Phorbol 12-myristate 13-acetate | 포볼12-미리스테이트 13-아세트산 |
| IL | Interleukin | 인터루킨 |
| mpk | mg/kg | 킬로그램 당 밀리그램 |
| H&E | Hematoxylin & Eosin | 헤마토실린과 에오신 |
| IHC | Immunohistochemistry | 면역조직화학염색 |

Test strains and vehicles used in the experiments of the present invention are shown in the table below.

1) Test Strain

TABLE 2

| | |
|---|---|
| Name | *B. pseudocatenulatum* C-RAPO (KCTC13986BP) |
| Production No. | 201908 |
| Date of purchase | 2019 Sep. 4 |
| Amount of purchase | 80 tubes |
| Phase | Ivory powder |
| Content | 10~15 mg /tube |
| Valid date | 2021.08 |
| Storage conditions | −70 degrees |
| Manufacturer | Bifido Co. Ltd. |
| Deposition No. | KCTC13986BP |
| Published | Published under Korean Patent Application No. 10-2019-0126394 |

TABLE 3

| | |
|---|---|
| Name | *B. bifidum* ATT (KCTC13474BP) |
| Production No. | 201908 |
| Date of purchase | 2019 Sep. 4 |
| Amount of purchase | 80 tubes |
| Phase | Ivory powder |
| Content | 10~15 mg /tube |
| Valid date | 2021.08 |
| Storage conditions | −70 degrees |
| Manufacturer | Bifido Co. Ltd. |
| Deposition No. | KCTC13474BP |
| Published | Published under Korean Patent Application 10-2018-0012354 |

TABLE 4

| | |
|---|---|
| Name | *B. longum* RAPO (KCTC13773BP) |
| Production No. | 201908 |
| Date of purchase | 2019 Sep. 4 |
| Amount of purchase | 80 tubes |
| Phase | Ivory powder |
| Content | 10~15 mg /tube |
| Valid date | 2021.08 |
| Storage conditions | −70 degrees |
| Manufacturer | Bifido Co. Ltd. |
| Deposition No. | KCTC13773BP |
| Published | Published under Korean Patent Application 10-2018-0160170 |

2) Vehicle

TABLE 5

| | |
|---|---|
| Name | Physiological saline |
| Production No. | KAH5134 3B |
| Manufacturer | ChoongWae Pharma Corporation |
| Storage conditions | Stored at room temperature |

The materials for the experiment of the present invention were tested under the following information conditions.

1) Test Animal Information

TABLE 6

| | |
|---|---|
| Species and lineage | NOD/ShiLtj mouse |
| Supply source | Central Experimental Animal Co., Ltd. |
| The reason for selection | This is a multiple model that causes type 1 diabetes. Diabetes occurring in this mouse is characterized by insulitis and causes lymphatic inflammation in the pancreas. At about 12 weeks of age, insulin secretion decreases rapidly, and this |

TABLE 6-continued

| | |
|---|---|
| | phenomenon progresses faster in females. As a result, the concentration of glucose in the plasma reaches 250 mg/dL only for subjects with diabetes. From about 12 weeks of age, salivary gland epithelial cells that secrete the salivary gland begin to deform, and at the age of 16 weeks, lymphocytic inflammation becomes serious and saliva secretion decreases. This is the reason for selection as an animal model for Sjogren's syndrome. |
| Date of purchase | 2019 Aug. 29 |
| Gender | Female |
| Number of animals and body weight range upon purchase | 40, 19-21 g |
| Number of animals and body weight range upon administration start | 40, 22-24 g |

2) Determination for Test Group Configuration
(1) Composition of Test Group

TABLE 7

| Group | Gender | Number of animals (No.) | Animal No. | Administration route/frequency | Amount of administered solution | Dose (mg/kg) |
|---|---|---|---|---|---|---|
| G1 Vehicle | Female | 8 | V | Oral administration once/day, 45 in total | 100 μL/ 20~25 g | — |
| G2 *B. pseudocatenulatum* C-RAPO | Female | 8 | L | | | 50 mg/kg |
| G3 *B. longum* RAPO | Female | 8 | R | | | 50 mg/kg |
| G4 *B. bifidum* ATT | Female | 8 | A | | | 50 mg/kg |

(2) Number of Subject

TABLE 8

| Subject marking | | | | | | | | |
|---|---|---|---|---|---|---|---|---|
| Vehicle (V) | 1X | 1L | 1R | 1B | 2X | 2L | 2R | 2B |
| C-RAPO(L) | 1X | 1L | 1R | 1B | 2X | 2L | 2R | 2B |
| RAPO(R) | 1X | 1L | 1R | 1B | 2X | 2L | 2R | 2B |
| ATT(A) | 1X | 1L | 1R | 1B | 2X | 2L | 2R | 2B |

(3) Grouping

Prior to administration of test substances *B. pseudocatenulatum* C-RAPO (KCTC13986BP), *B. longum* RAPO (KCTC13773BP) and *B. bifidum* ATT (KCTC13474BP), grouping was performed based on the results of SFR measurement of NOD/ShiLtJ mice 10 weeks of age, before significant reduction in salivation. The amount of saliva (μL) (SFR) obtained through pilocarpine activation for 10 minutes was calculated and compared as a function of body weight (g) and time (minute). Grouping was conducted as uniformly as possible such that the mean and standard deviation of SFR at 10 weeks of age were G1: 0.673±0.120 μL/g/min, G2: 0.672±0.120 μL/g/min, G3: 0.671±0.129 μL/g/min, G4: 0.673±0.133 μL/g/min.

Figure 1:
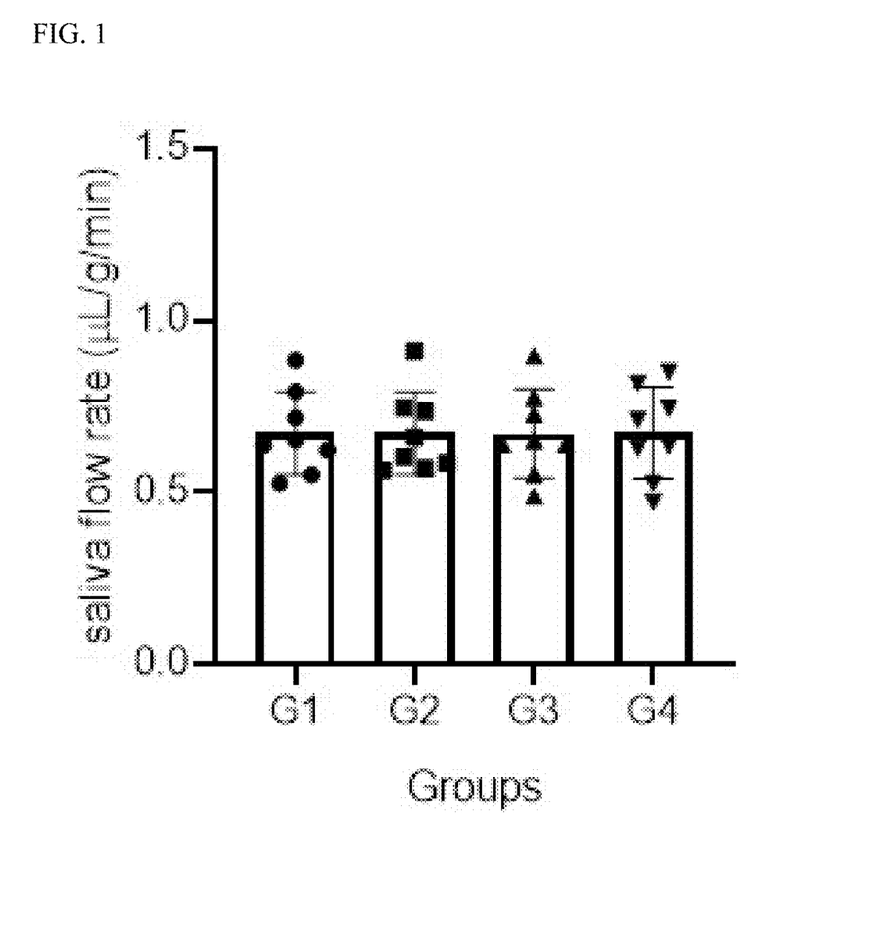
FIG. 1 shows grouping as a function of saliva flow rate (SFR) at 10 weeks of age according to the present invention.

Grouping as a function of saliva flow rate (SFR) at 10 weeks of age is shown in FIG. 1. FIG. 1 shows grouping as a function of saliva flow rate (SFR) at 10 weeks of age according to the present invention. That is, after measurement of saliva flow rate (SFR), 10-week-old animals were divided such that the mean saliva flow rate in each group and the standard deviation (SD) for each group were distributed as uniformly as possible, to construct "configuration of test groups" (Table 7).

(4) Preparation of Administered Substance

The test substance was dispensed at a dose of 10 to 15 mg/tube, incorporated and then diluted in physiological saline at a concentration of 10 mg/ml immediately before administration. The test substance was prepared in the corresponding dose daily and the remaining substance was immediately discarded. Injection of the test substance was started the following day after measuring the saliva flow rate at 10 weeks of age.

(5) Administration

Vehicles and test substances were orally administered through the intended clinical route for application to humans. The test substance for oral administration was administered directly into the stomach using a syringe equipped with a sonde for oral administration. In addition, a substance for injection (saliva-inducing substance, pilocarpine) was directly intraperitoneally administered at a dose of 0.1 mg/100 μL after manual calibration on mice.

(6) Frequency and Time of Administration

The vehicles and test substances were administered once a day, 45 times in total over 9 weeks. The saliva-inducing substance (pilocarpine) was administered once or twice a week (when saliva flow rate (SFR) was analyzed, some subjects were measured again the next day), and the mice were given unlimited access to feed.

3) Test Method and Test Items (1) Weight Measurement

Measurements were conducted at intervals of 2 weeks from 10 weeks to 18 weeks of age.

(2) Immunoglobulin Analysis

Orbital blood was collected every two weeks from 10 weeks to 18 weeks of age and serum obtained therefrom was used for measurement. Serum was used for measurement after 50,000-fold dilution with Tris buffer solution containing 1% bovine serum albumin. The products used for ELISA measurement were as follows, and measurements were performed according to the manufacturer's recommendation.

TABLE 9

| Sample name | Manufacturer | Cat. No | Dose |
|---|---|---|---|
| Mouse IgG ELISA Quantitation set | Bethyl lab. | E90-131 | 1 |
| TMB substrate solution | ThermoFisher | 00-4201-56 | 1 |

(3) Saliva Flow Rate (SFR) Analysis

Preparation of saliva-inducing substance: Pilocarpine hydrochloride (Sigma, Cat. No. P6503) was dissolved at a concentration of 1 mg/ml in distilled water and the resulting solution was filtered through a 0.22 μm syringe filter.

Saliva collection: mice were subjected to respiratory anesthesia with isoflurane for 1 minute immediately after intraperitoneal injection of a pilocarpine solution at 0.1 ml/mouse. Each mouse was calibrated by hand and saliva collected in the mouth of the mouse was collected in a tube using a 200 μL micropipette for 10 minutes. The collected saliva was centrifuged at 8,000 rpm for 5 minutes and then the volume was measured and recorded using a 200 μL micropipette. The saliva flow rate was calculated as saliva (μL)/body weight (g)/1 minute and compared. The separated saliva supernatant was frozen at −20° C. Subjects having a saliva flow rate (SFR) below the average in the group were measured again and calibrated the next day.

(4) Tissue Analysis (Hematoxylin & Eosin)

After euthanasia of each of the 18-week-old mice, the neck thereof was excised and the salivary glands were extracted and immobilized by soaking in formalin solution, and then produced into a paraffin block. Hematoxylin & Eosin staining was performed on three salivary gland section slides from each of three sites. After 40× magnification microscopy, foci of 20 or more lymphocytes in tissues were counted and scored.

Inflammation scoring: 0 Points: no foci; 1 Point: 1 focus; 1.5 Points: 2 foci; 2~2.5 Points: 3~5 foci; 3 Points: 6~9 foci.

(5) Immunohistochemistry (T Cell/B Cell Analysis, IHC)

After euthanasia of each 18-week-old animal, the salivary gland was extracted to produce a paraffin block. IHC was performed on one piece from each of the slides of all tested salivary gland sections. As an antibody, anti-CD3 (Abcam Cat. No. ab16669) was used for T cell detection and anti-B220 (BD Cat. No. 550286) was used for B cell detection. After imaging each focus in a slide under a 200× microscope, the positive region of CD3 or B220 stained in brown was masked using Image J software (NIG, Md., USA). The area of CD3 or B220 in the microscopic field with foci was calculated as the number of pixels, the area having no foci was treated as 0, and the average area of CD3 or B220 was compared between groups.

(6) Flow Cytometry

In the 18-week-old animal model into which the test drug was injected, cells were separated from blood obtained using a heparin-treated capillary tube, and red blood cells were removed with ACK lysis buffer, suspended in 10% RPMI1640 medium, and then stimulated with PMA, ionomycin, and monensin (BD GolgiStop) for 4 hours. The cells were recovered, washed, stained with fixable viability dye-e780, CD3-Pacific Blue and CD4-PerCP/Cy5.5, subjected to permeabilization and then reacted with IL-17A-FITC antibody. Lymphocytes in FSC-A vs. SSC-A and live cells (e780 negative) in FSC-A vs. fixable viability dye eFluor780 were gated, and CD3+CD4+IL-17A$^+$ cells were analyzed (BD LSRII Fortessa).

TABLE 10

| Sample name | Manufacturer | Cat. No | Dose |
|---|---|---|---|
| PMA | Sigma-Aldrich | P8139 | 25 ng/mL |
| Ionomycin | Sigma-Aldrich | I0634 | 250 ng/mL |
| GolgiStop | BD biosciences | 554724 | 0.67 μL/$10^6$ cells/mL |
| Fixable viability dye eFlour780 | Thermo | 65-0865-18 | 0.1 μL/$10^6$ cells |
| Anti-mouse CD3 V450 | Thermo | 48-0033-82 | 0.25 μg/test |
| Anti-mouse CD4 PerCP/Cy5.5 | Thermo | 45-0042-82 | 0.25 μg/test |
| Anti-mouse IL-17A Alexa488 | BioLegend | 506910 | 0.25 μg/test |

(7) Statistical Method

All data are expressed as mean and standard deviation (mean±SD) and a Mann-Whitney test was performed using a GraphPad PRISM Version 8.2 (GraphPad Software, USA) analysis program for comparison between two groups, namely a vehicle-administered group and a test-substance-administered group. The case of P≤0.05 was determined to be statistically significant.

Example 1: Salivary Tissue Pathology Analysis-H&E Staining Analysis after Administration of *B. pseudocatenulatum* C-RAPO (KCTC13986BP) and *B. bifidum* ATT (KCTC13474BP)

In this example, testing was conducted to evaluate the effect of administration of the selected strains, *B. pseudocatenulatum* C-RAPO (KCTC13986BP), *B. longum* RAPO (KCTC13773BP) and *B. bifidum* ATT (KCTC13474BP) on inflammatory infiltration in salivary gland tissue of NOD/ShiLtJ mice.

The salivary gland tissue of the 18-week-old mouse was analyzed. After completion of the 18-week-old mouse test, the mice were euthanized and the salivary glands were extracted therefrom to produce a paraffin block. Hematoxylin & Eosin staining was performed on all three salivary gland section slides spaced at a distance of 100 μm or more. Then, areas where foci of 20 or more lymphocytes were observed were imaged at 40× magnification, and the number of foci was counted and was digitized to obtain an inflammation score in accordance with the criteria and comparatively analyzed.

Inflammation scoring: 0 Points: no foci; 1 Point: 1 focus; 1.5 Points: 2 foci; 2~2.5 Points: 3~5 foci; 3 Points: 6~9 foci. The results of analysis of the number of foci per unit area in salivary gland tissue showed 9±2 in the V group, 5±3 in the C-RAPO group, and 7±4 in the ATT group (FIG. 2).

Figure 2:
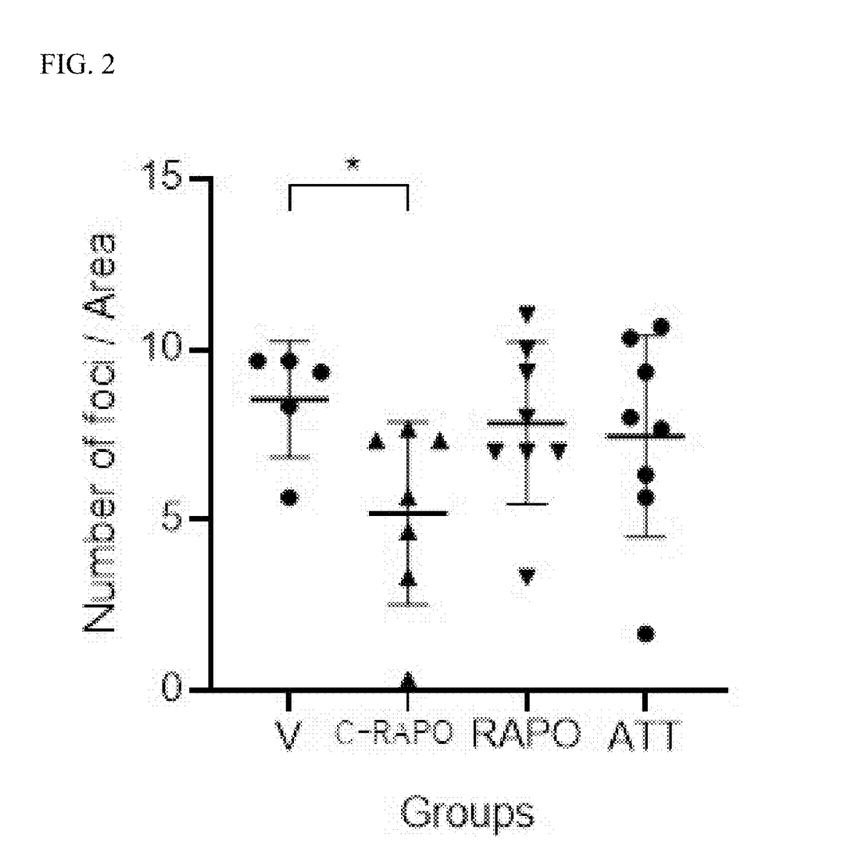
FIG. 2 is a graph showing the number of foci per unit area in salivary gland tissue after administration of vehicles and test substances of the present invention.
Figure 3:
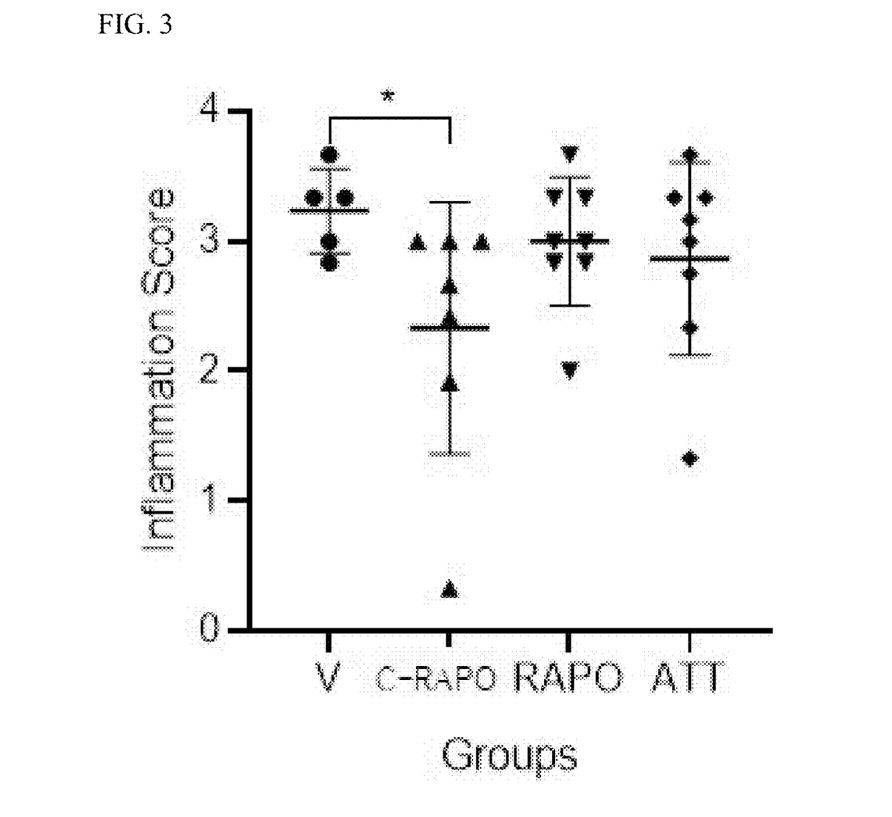
FIG. 3 is a graph showing an inflammation score converted from the number of foci per unit area in the salivary gland tissue after administration of the vehicle and test substances of the present invention.

FIG. 2 is a graph showing the number of foci per unit area in salivary gland tissue after administration of vehicles and test substances of the present invention. When converting the number of foci to the inflammation score, inflammation scores were 3.2±0.50 for V, 2.3±0.99 for C-RAPO, 3.2±0.49 for RAPO, and 2.8±0.94 for ATT, and the resulting values were expressed as mean±standard deviation (FIG. 3). FIG. 3 is a graph showing an inflammation score converted from the number of foci per unit area in the salivary gland tissue after administration of the vehicles and test substances of the present invention.

Figure 4:
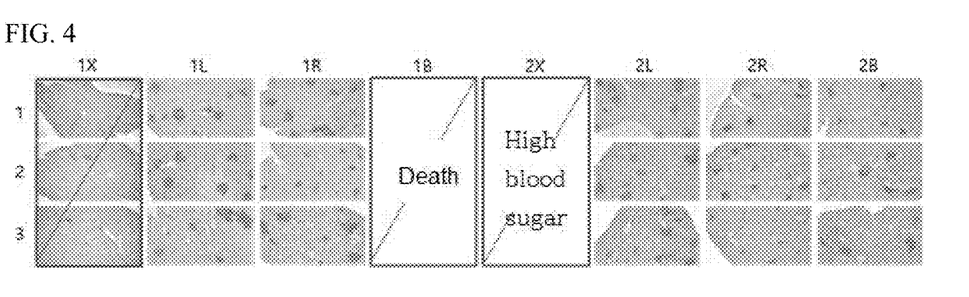
FIG. 4 is an image showing the salivary tissue slide at 40× magnification of the vehicle-administered group (Vehicle) as a result of salivary tissue pathological analysis of the present invention (H&E)
Figure 5:
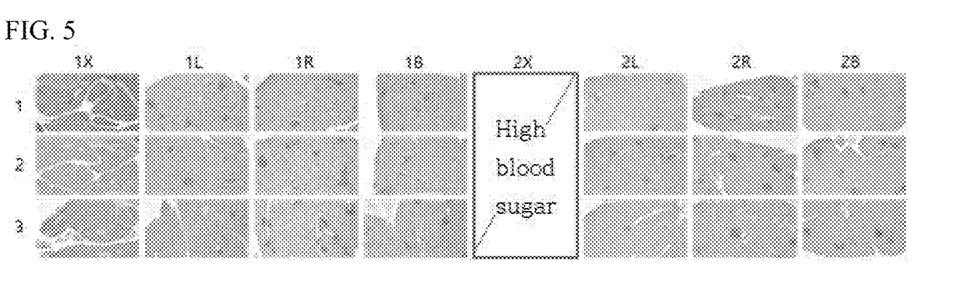
FIG. 5 is an image showing the salivary tissue slide at 40× magnification of the *B. pseudocatenulatum* C-RAPO-administered group as the result of salivary tissue pathological analysis of the present invention (H&E)
Figure 6:
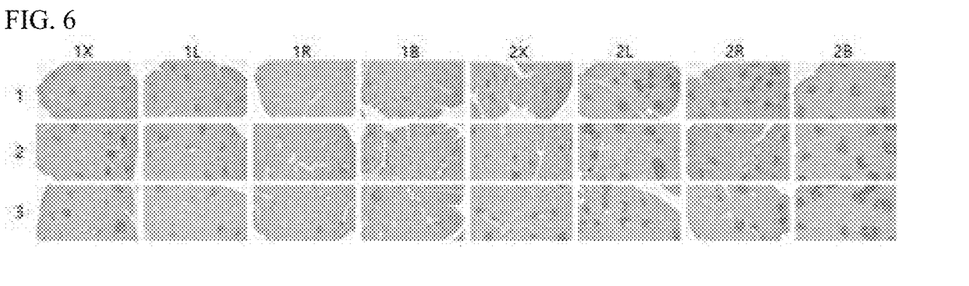
FIG. 6 is an image showing the salivary tissue slide at 40× magnification of the *B. longum* RAPO-administered group as a result of salivary tissue pathological analysis of the present invention (H&E)
Figure 7:
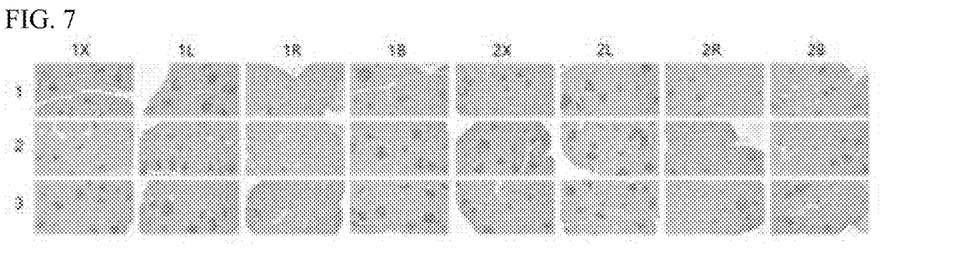
FIG. 7 is an image showing the salivary tissue slide at 40× magnification of the *B. bifidum* ATT-administered group as a result of salivary tissue pathological analysis of the present invention (H&E)

FIG. 4 is an image showing the salivary tissue slide at 40× magnification of the vehicle-administered group (Vehicle) (1, 2 and 3 on the vertical axis in FIG. 4 indicate the sample numbers, the experiment was conducted in triplicate and the same applies to the image below) as a result of salivary tissue pathological analysis of the present invention (H&E). FIG. 5 is an image showing the salivary tissue slide at 40× magnification of the *B. pseudocatenulatum* C-RAPO (KCTC13986BP)-administered group as the result of salivary tissue pathological analysis of the present invention. FIG. 6 is an image showing the salivary tissue slide at 40× magnification of the *B. longum* RAPO (KCTC13773BP)-administered group as the result of salivary tissue pathological analysis of the present invention. FIG. 7 is an image showing the salivary tissue slide at 40× magnification of the *B. bifidum* ATT (KCTC13474BP)-administered group as the result of salivary tissue pathological analysis of the present invention.

The result of statistical analysis of this experiment demonstrated that therapeutic efficacy for sialoadenitis appeared in the *B. pseudocatenulatum* C-RAPO (KCTC13986BP)-administered group.

Example 2: Salivary Tissue Pathology Analysis-Analysis of T-Cell/B-Cell Infiltration in Salivary Gland Tissue after Administration of *B. pseudocatenulatum* C-RAPO (KCTC13986BP) and *B. bifidum* ATT (KCTC13474BP)

In this example, the salivary gland tissue of the 18-week-old mice was analyzed to evaluate the effect of administration of the selected strains, *B. pseudocatenulatum* C-RAPO (KCTC13986BP), *B. longum* RAPO (KCTC13773BP) and *B. bifidum* ATT (KCTC13474BP) on infiltration of immune cells (T cells and B cells) in salivary gland tissue of NOD/ShiLtJ mice.

After completion of the 18-week-old mouse test, the mice were euthanized and the salivary gland was extracted to produce a paraffin block. One of each salivary gland tissue slide was stained by immunohistochemistry (IHC) using a CD3 (T cell marker) or B220 (B cell marker) antibody. After imaging each focus in the slide on a 200× microscope, the region of CD3 (T cell) or B220 (B cell) marked in brown in each focus was calculated as the number of pixels using Image J software (NIG, Md., USA), the area having no foci was represented as "0", and the average thereof was compared. The representative staining result for each subject is shown one by one.

Figure 8:
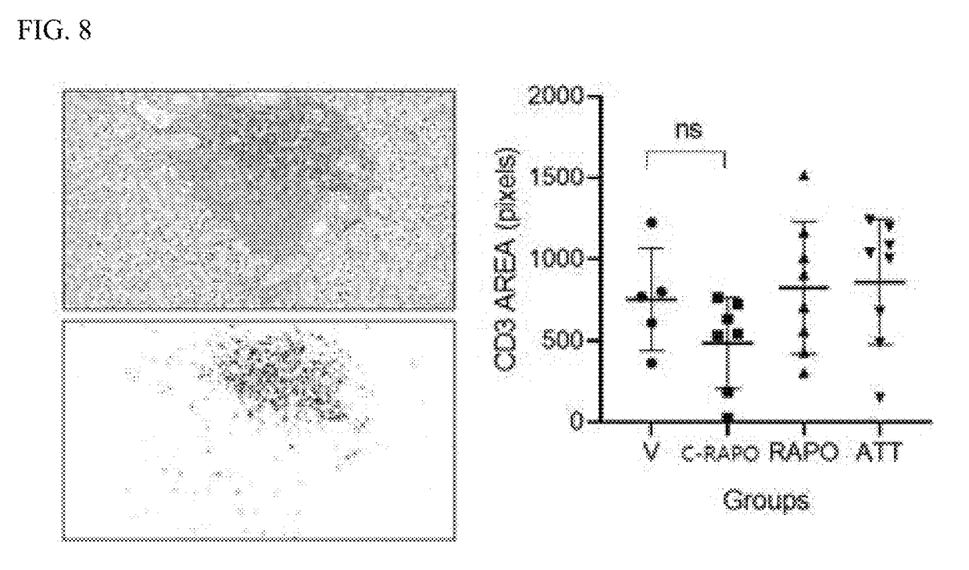
FIG. 8 shows the result of B cell infiltration in salivary gland tissue, wherein the salivary gland tissue of an 18-week-old mouse was extracted and produced into a paraffin block, the tissue fragment was stained by immunohistochemistry with CD3 antibody and imaged under a microscope at 200× magnification, the positive site was masked in black (left in FIG. 8) using Image J software, the number of pixels was calculated and the CD3 positive area per unit area was expressed as the mean±standard deviation (right in FIG. 8)

Meanwhile, the result of analysis of T cell infiltration area per unit area in salivary gland tissue (FIG. 8) was 755±314.8 pixels for V (control group), 488±277.8 pixels for the *B. pseudocatenulatum* C-RAPO-administered group, 826±404.5 pixels for the *B. longum* RAPO-administered group, and 862±384.6 pixels for the *B. bifidum* ATT-administered group. The result of statistical analysis showed that the *Bifidobacterium pseudocatenulatum* C-RAPO (KCTC13986BP)-administered group inhibits T cell infiltration in the salivary gland tissue. FIG. 8 shows the result of B cell infiltration in salivary gland tissue. The salivary gland tissue of an 18-week-old mouse was extracted and produced into a paraffin block, the tissue fragments were stained by immunohistochemistry with CD3 antibody and imaged under a microscope at 200× magnification, the positive site was masked in black (left in FIG. 8) using Image J software, and the number of pixels was calculated. The CD3 positive area per unit area was expressed as the mean±standard deviation (right in FIG. 8, ns (non-significant) in the graph means no significance, the same applies to the graph below).

Figure 9:
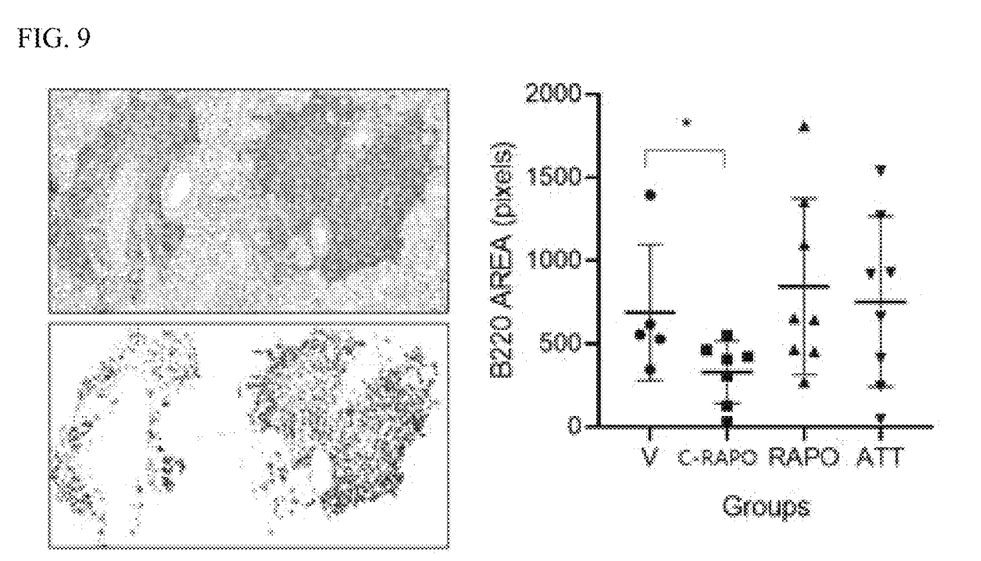
FIG. 9 shows the result of B cell infiltration in salivary gland tissue, wherein the salivary gland tissue of an 18-week-old mouse was extracted and produced into a paraffin block, the tissue fragment was stained by immunohistochemistry (IHC) with B220 antibody and imaged under a microscope at 200× magnification, the positive site was masked in black (left in FIG. 9) using Image J software, the number of pixels was calculated, the B220 positive area per unit area was expressed as the mean±standard deviation (right in FIG. 9)

Meanwhile, the result of analysis of B cell infiltration area per unit area in salivary gland tissue (FIG. 9) was 689±406.9 pixels for V (control group), 331±187.6 pixels for the *B. pseudocatenulatum* C-RAPO-administered group, 844±527.9 pixels for the *B. longum* RAPO-administered group, and 753±510.5 pixels for the *B. bifidum* ATT-administered group. The result of statistical analysis showed that the *Bifidobacterium pseudocatenulatum* C-RAPO (KCTC13986BP)-administered group inhibits B cell infiltration in the salivary gland tissue (V vs. C-RAPO, *P<0.05). FIG. 9 shows the result of B cell infiltration in salivary gland tissue. The salivary gland tissue of an 18-week-old mouse was extracted and produced into a paraffin block, the tissue fragment was stained by immunohistochemistry (IHC) with B220 antibody and imaged under a microscope at 200× magnification, the positive site was masked in black (left in FIG. 9) using Image J software, and the number of pixels was calculated. The B220 positive area per unit area was expressed as the mean±standard deviation (right in FIG. 9).

The experimental results described above showed that *B. pseudocatenulatum* C-RAPO (KCTC13986BP) administered at a dose of 50 mg/kg/day has effects of reducing inflammatory cell infiltration in salivary gland tissue, and reducing infiltration of T and B cells (particularly, significantly reducing B cell infiltration). This demonstrate that *B. pseudocatenulatum* C-RAPO (KCTC13986BP) has an inhibitory effect against sialoadenitis.

Example 3: Analysis of Saliva Flow Rate after Administration of *B. pseudocatenulatum* C-RAPO (KCTC13986BP) and *B. bifidum* ATT (KCTC13474BP)

In this test, the saliva flow rate per minute was measured and digitized to evaluate the effect of administration of the selected strains, *B. pseudocatenulatum* C-RAPO (KCTC13986BP), *B. longum* RAPO (KCTC13773BP) and *B. bifidum* ATT (KCTC13474BP) on the ability of NOD/ShiLtJ mice to secrete saliva.

Figure 10:
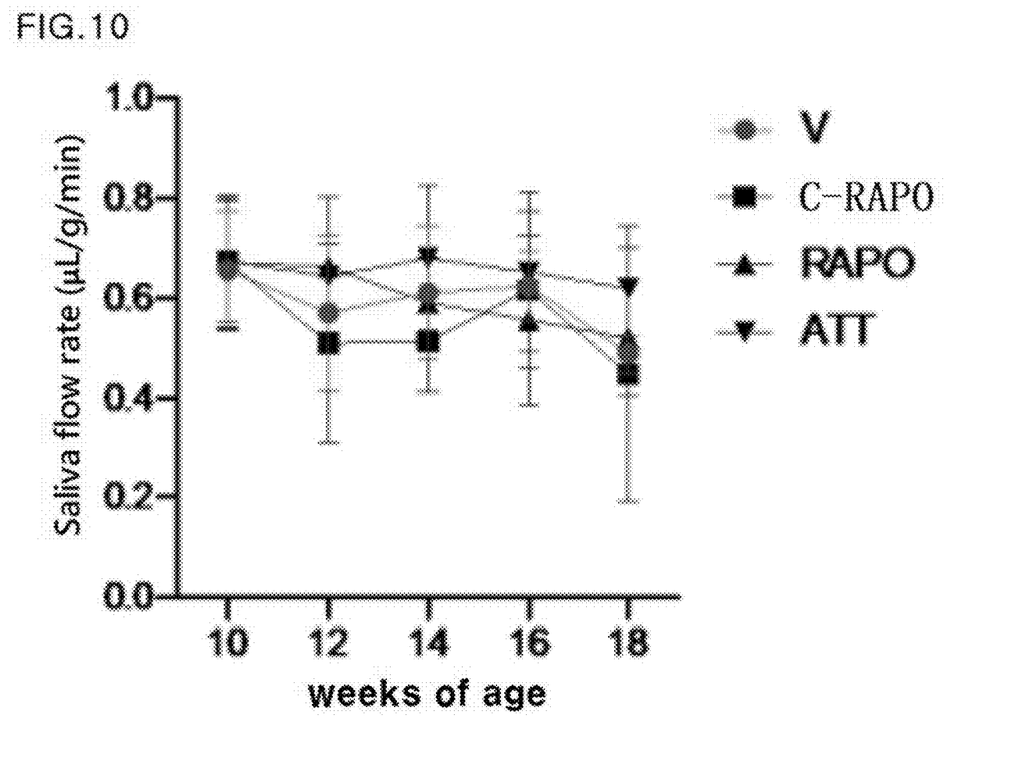
FIG. 10 is a graph showing the result of quantification of the effect on saliva secretion function by measurement of the amount of saliva secreted by NOD/ShiLtJ mice depending on age (weeks) in response to administration of the vehicle and test substances of the present invention.

FIG. 10 is a graph showing the result of quantification of the effect on saliva secretion function by measurement of the amount of saliva secreted by NOD/ShiLtJ mice depending on age (weeks) in response to administration of the vehicle and test substances of the present invention.

Figure 11:
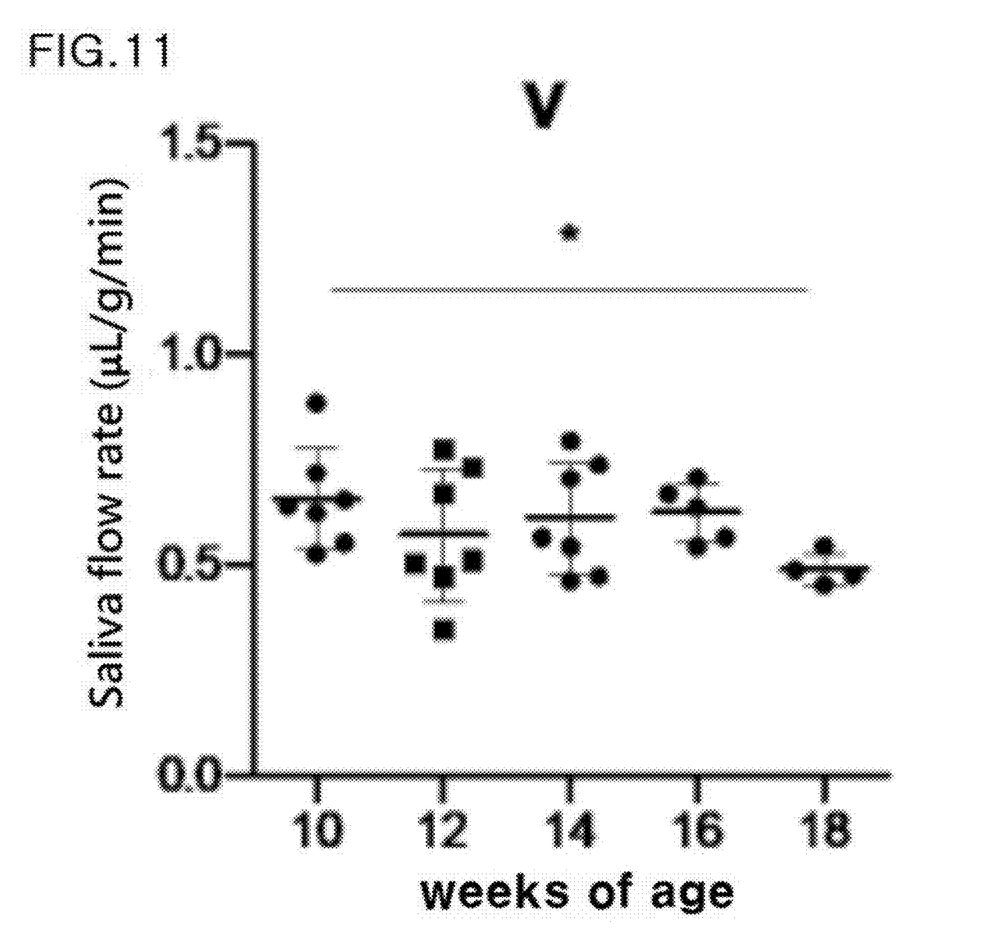
FIG. 11 is a graph showing the amount of saliva secreted (SFR) by the vehicle group of the present invention as a function of age (weeks), digitized as the amount of saliva secreted by a subject.
Figure 12:
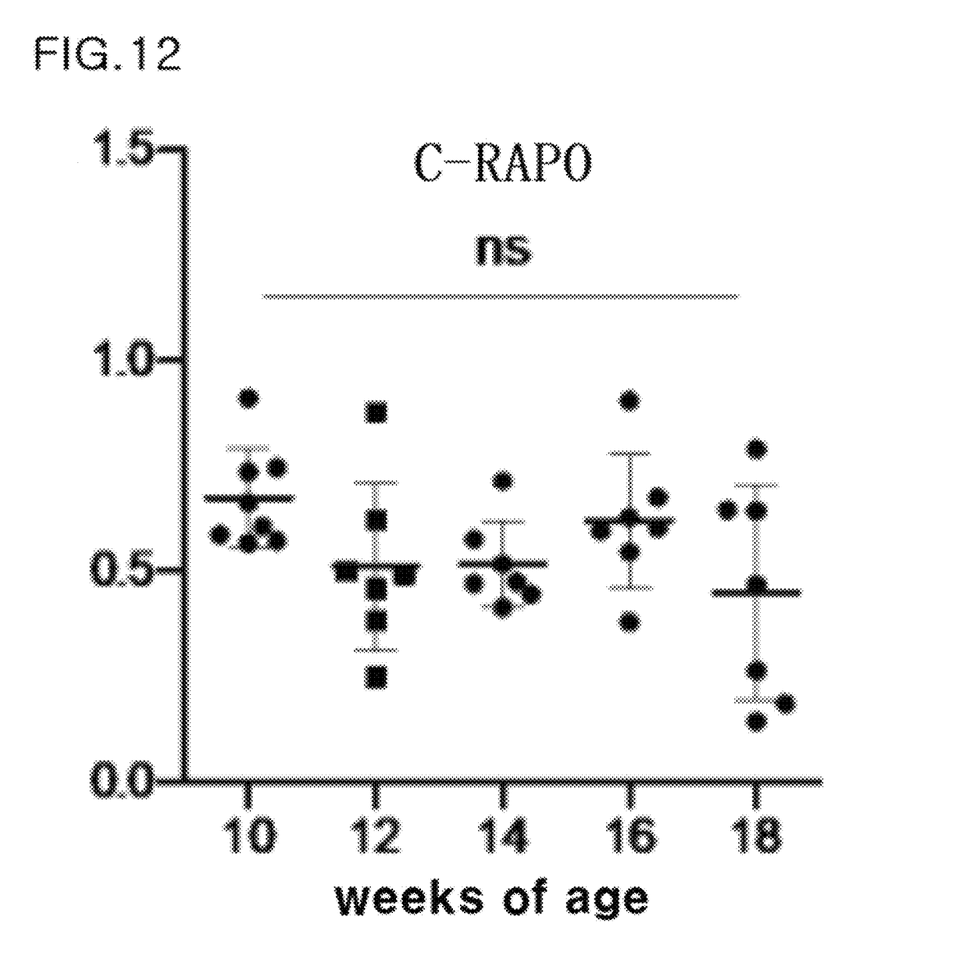
FIG. 12 is a graph showing the amount of saliva secreted (SFR) by the C-RAPO group of the present invention as a function of age (weeks) digitized as the amount of saliva secreted by a subject.
Figure 13:
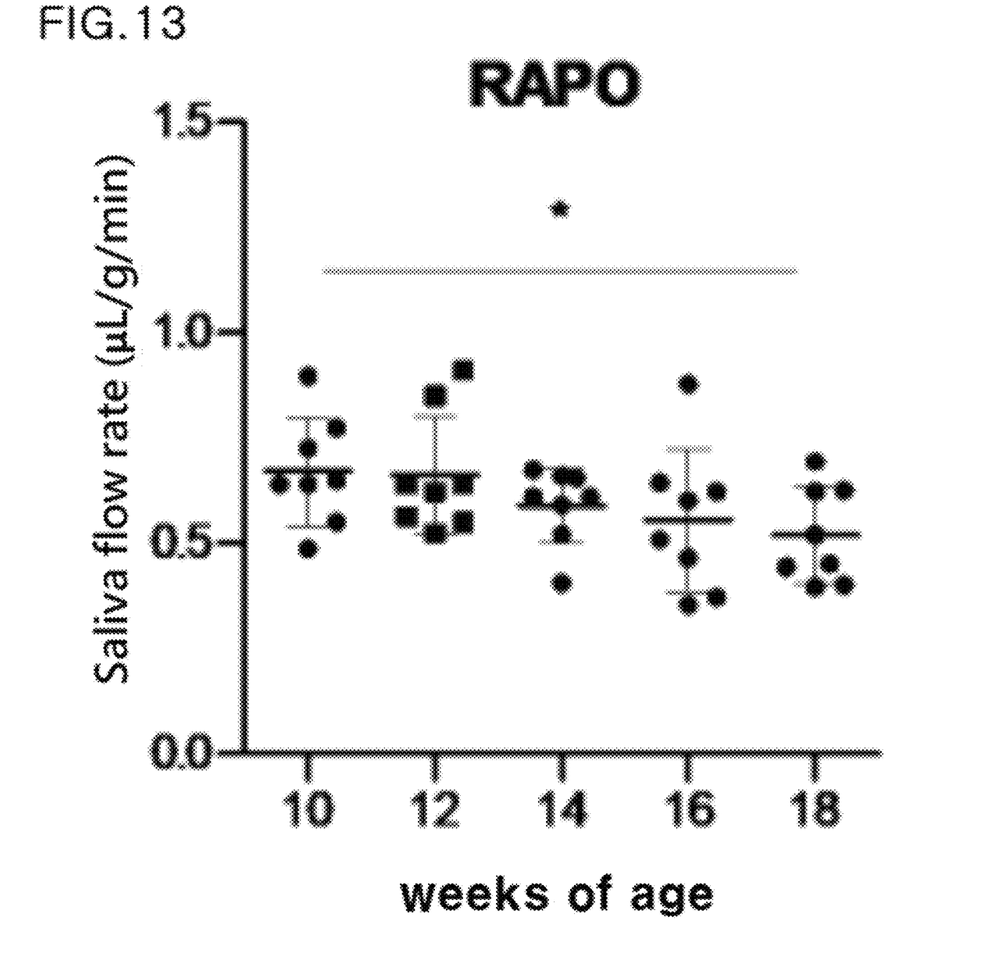
FIG. 13 is a graph showing the amount of saliva secreted (SFR) by the RAPO group of the present invention as a function of age (weeks), digitized as the amount of saliva secreted by subject.
Figure 14:
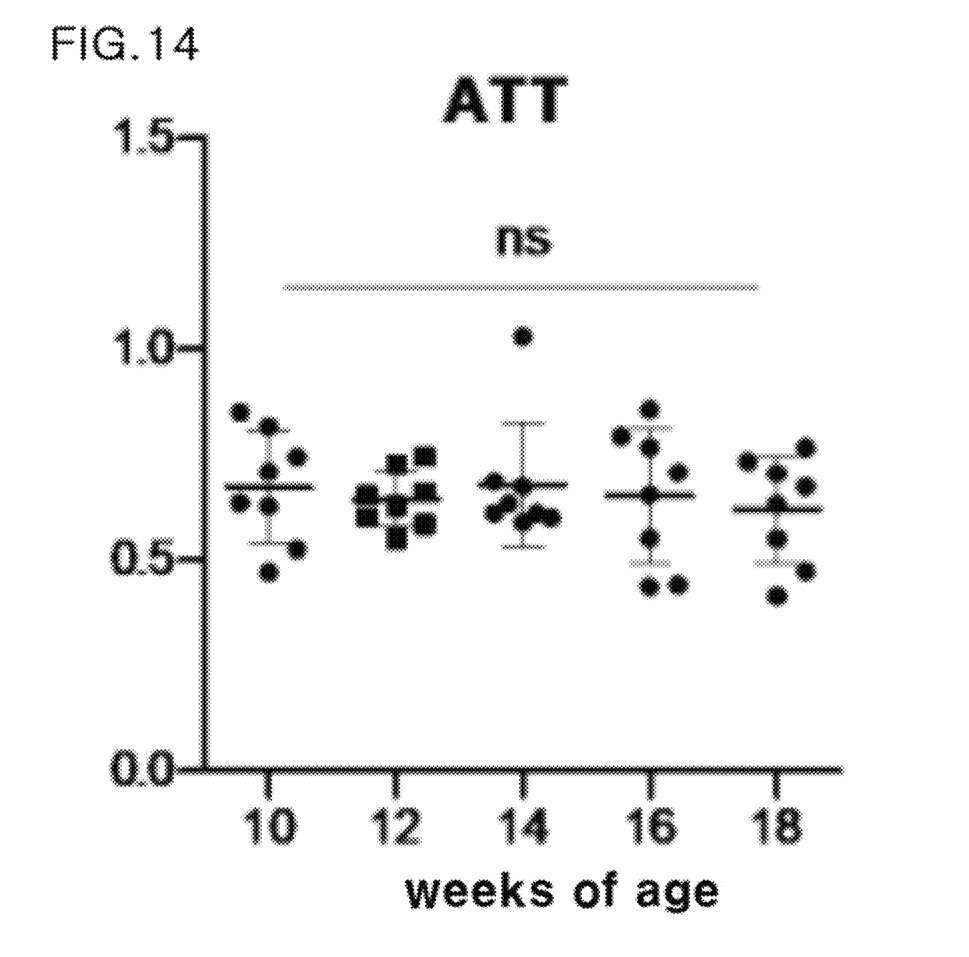
FIG. 14 is a graph showing the amount of saliva secreted (SFR) by the ATT group of the present invention as a function of age (weeks), digitized as the amount of saliva secreted by a subject.

In addition, FIG. 11 is a graph showing the amount of saliva secreted by the vehicle group of the present invention as a function of age (weeks), digitized as the amount of saliva secreted by a subject. FIG. 12 is a graph showing the amount of saliva secreted by the C-RAPO group of the present invention as a function of age (weeks) digitized as the amount of saliva secreted by a subject. FIG. 13 is a graph showing the amount of saliva secreted by the RAPO group of the present invention as a function of age (weeks), digitized as the amount of saliva secreted by subject. FIG. 14 is a graph showing the amount of saliva secreted by the ATT group of the present invention as a function of age (weeks), digitized as the amount of saliva secreted by a subject. As can be seen from FIG. 11, the saliva flow rate after vehicle (V) administration was measured at 2-week intervals from 10 weeks to 18 weeks of age, monitoring of saliva flow rate was started from 10 weeks of age, SFR at 10 weeks of age was 0.673±0.12, SFR at 18 weeks of age was 0.489±0.039 µL/g/min, and the saliva flow rate at 18 weeks was significantly decreased compared to the initial saliva flow rate at 10 weeks (FIG. 12, 18 w compared to 10 w, *P<0.05). These results demonstrated that the saliva flow rate was significantly reduced by the administration of a vehicle (V), and showed that the Sjogren's syndrome model, which should exhibit reduced saliva secretion over time, functions normally.

In addition, as can be seen from FIG. 12, administration with *B. pseudocatenulatum* C-RAPO (KCTC13986BP) decreased SFR (more particularly, SFR was 0.672±0.12 µL/g/min at 10 weeks of age, and SFR was 0.520±0.114 µL/g/min at 18 weeks of age), but no statistical significance was detected (ns means no significance). These results indicate that the C-RAPO strain had no significant difference in the amount of secreted saliva at 18 weeks compared to initially, at 10 weeks, and the C-RAPO strain is capable of inhibiting a reduction in the amount of secreted saliva, that is, a reduction in the amount of secreted saliva due to Sjogren's syndrome. In addition, as can be seen from FIG. 13, administration with *B. longum* RAPO (KCTC 13773BP) decreased SFR (more particularly, SFR was 0.671±0.129 µL/g/min at 10 weeks of age, and was 0.447±0.254 µL/g/min at 18 weeks of age), but the decrease in SFR was statistically significant (FIG. 14, 18 w compared to 10 w, *P<0.05). These results demonstrated that administration of RAPO did not inhibit reduction in the amount of secreted saliva and thus RAPO is incapable of inhibiting the reduction of the amount of saliva due to Sjogren's syndrome.

In addition, as can be seen from FIG. 14, SFR upon administration of *B. bifidum* ATT (KCTC13474BP) was 0.673±0.133 µL/g/min at 10 weeks of age, and 0.619±0.127 µL/g/min at 18 weeks of age, but no statistical significance was detected (ns means no significance). These results indicate that the ATT strain had no significant difference in the amount of secreted saliva at 18 weeks compared to the initial saliva flow rate at weeks, and the ATT strain is capable of inhibiting a reduction in the amount of secreted saliva, that is, a reduction in the amount of secreted saliva due to Sjogren's syndrome.

The result of the saliva flow rate experiment showed that administration with a dose of 50 mg/kg/day of *B. pseudocatenulatum* C-RAPO (KCTC13986BP) and *B. bifidum* ATT (KCTC13474BP) inhibits the reduction of saliva flow rate.

It can be seen from the above results that the strains *B. pseudocatenulatum* C-RAPO (KCTC13986BP) and *B. bifidum* ATT (KCTC13474BP) of the present invention have the effects of inhibiting sialoadenitis, which is a symptom of the Sjogren's syndrome, and inhibiting a reduction in saliva flow rate.

As is apparent from the foregoing, the *Bifidobacterium pseudocatenulatum* C-RAPO (KCTC13986BP) and *Bifidobacterium bifidum* ATT (KCTC13474BP) strains according to the present invention have the effects of inhibiting sialoadenitis, which is a symptom of the Sjogren's syndrome, and inhibiting a reduction in saliva flow rate. Based on this, the present invention can be used for prevention or treatment of Sjogren's syndrome and enables development of food, health food and pharmaceuticals.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of inhibiting sialoadenitis symptom in a subject having Sjogren's syndrome comprising administering orally to said subject a food composition comprising an effective amount of an isolated strain of *Bifidobacterium bifidum* ATT deposited as KCTC13474BP.

2. A method of treating a subject having Sjogren's syndrome comprising administering orally to said subject a food composition comprising an effective amount of an isolated strain of *Bifidobacterium bifidum* ATT deposited as KCTC13474BP, wherein reduction of saliva secretion is inhibited in the subject.

3. A method of inhibiting sialoadenitis symptom in a subject having Sjogren's syndrome comprising administering orally to said subject a pharmaceutical composition comprising an effective amount of an isolated strain of *Bifidobacterium bifidum* ATT deposited as KCTC13474BP.

4. A method of treating a subject having Sjogren's syndrome comprising administering orally to said subject a pharmaceutical composition comprising an effective amount of an isolated strain of *Bifidobacterium bifidum* ATT deposited as KCTC13474BP, wherein reduction of saliva secretion is inhibited in the subject.

* * * * *